United States Patent
Bancaud et al.

(10) Patent No.: US 11,262,333 B2
(45) Date of Patent: Mar. 1, 2022

(54) METHOD AND DEVICE FOR CONCENTRATING MOLECULES OR OBJECTS DISSOLVED IN SOLUTION

(71) Applicant: CENTRE NATIONAL DE LA RECHERCHE SCIENTIFIQUE, Paris (FR)

(72) Inventors: Aurélien Bancaud, Toulouse (FR); Hubert Ranchon, Toulouse (FR); Thierry Leichle, Toulouse (FR); Pattamon Teerapanich, Toulouse (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 411 days.

(21) Appl. No.: 15/500,508

(22) PCT Filed: Aug. 3, 2015

(86) PCT No.: PCT/EP2015/067826
§ 371 (c)(1),
(2) Date: Jan. 30, 2017

(87) PCT Pub. No.: WO2016/016470
PCT Pub. Date: Feb. 4, 2016

(65) Prior Publication Data
US 2017/0227506 A1    Aug. 10, 2017

(30) Foreign Application Priority Data

Aug. 1, 2014   (FR) ...................................... 1457544

(51) Int. Cl.
*G01N 30/00* (2006.01)
*G01N 15/06* (2006.01)
(Continued)

(52) U.S. Cl.
CPC .......... *G01N 30/0005* (2013.01); *B01L 3/502* (2013.01); *B01L 3/502753* (2013.01);
(Continued)

(58) Field of Classification Search
CPC ......... B01L 3/502707; B01L 3/502715; B01L 3/50273; B01L 3/502753; B01L 3/502761;
(Continued)

(56) References Cited

U.S. PATENT DOCUMENTS 6,635,163 B1 * 10/2003 Han ...................... B01D 57/02
204/450
8,440,063 B2   5/2013 Han et al.
(Continued)

FOREIGN PATENT DOCUMENTS

JP       2004-217 A      1/2004
WO    2014/020271 A1   2/2014

OTHER PUBLICATIONS

Andriamanampisoa, et al., "BIABooster: Online DNA Concentration and Size Profiling with a Limit of Detection of 10 fg/µL and Application to High-Sensitivity Characterization of Circulating Cell-Free DNA", Anal. Chem., 90, pp. 3766-3774, 2018.
(Continued)

*Primary Examiner* — Gurpreet Kaur
(74) *Attorney, Agent, or Firm* — BakerHostetler

(57) ABSTRACT

A method for concentrating electrically charged objects in a non-Newtonian liquid medium comprises: feeding a sample containing electrically charged objects into a channel having a flow axis, a first transverse cross-section orthogonal to the flow axis, and at least one second transverse cross-section orthogonal to the flow axis, one dimension of the second cross-section being less than the corresponding dimension of the first cross-section; and applying a hydrodynamic flow in
(Continued)

a direction of the channel together with the application, in the opposite direction, of an electric field in the channel, thus making it possible to move the electrically charged objects in the channel along the flow axis from the first cross-section to the second cross-section, stop the objects, and concentrate the objects in at least one area upstream from the second transverse cross-section.

16 Claims, 9 Drawing Sheets

(51) Int. Cl.
| | | |
|---|---|---|
| *G01N 21/64* | (2006.01) | |
| *C12Q 1/68* | (2018.01) | |
| *G01N 27/447* | (2006.01) | |
| *B01L 3/00* | (2006.01) | |
| *C12Q 1/6806* | (2018.01) | |

(52) U.S. Cl.
CPC ........... *C12Q 1/6806* (2013.01); *G01N 15/06* (2013.01); *G01N 21/6458* (2013.01); *G01N 27/44791* (2013.01); *B01L 2300/0816* (2013.01); *B01L 2400/0421* (2013.01); *G01N 2015/0693* (2013.01); *G01N 2030/004* (2013.01)

(58) Field of Classification Search
CPC ..... B01L 2400/0421; B01L 2400/0487; B01L 2200/0652; B01L 2200/0684; B01L 2200/0668; B01L 2400/0684; B01L 2400/0668; G01N 27/44791; G01N 27/447; G01N 27/44769; G01N 15/06; G01N 21/6458; G01N 30/0005; G01N 2030/004; G01N 2030/0065; C12Q 1/6806
See application file for complete search history.

(56) References Cited

U.S. PATENT DOCUMENTS

| | | | |
|---|---|---|---|
| 8,753,492 B2 | 6/2014 | Ko et al. | |
| 8,783,466 B2 | 7/2014 | Han et al. | |
| 2001/0023825 A1* | 9/2001 | Frumin | G01N 27/44773 |
| | | | 204/458 |
| 2005/0126914 A1 | 6/2005 | Sibbett | |
| 2005/0258040 A1* | 11/2005 | Ross | G01N 27/44734 |
| | | | 204/450 |
| 2005/0284762 A1* | 12/2005 | Astorga-Wells | ............ |
| | | | B01L 3/502753 |
| | | | 204/451 |
| 2008/0087546 A1 | 4/2008 | Strand et al. | |
| 2014/0131204 A1* | 5/2014 | Chou | B03C 5/005 |
| | | | 204/452 |
| 2015/0360237 A1* | 12/2015 | Hayes | B01L 3/50273 |
| | | | 204/451 |

OTHER PUBLICATIONS

Astorga-Wells, et al., "Microfluidic Electrocapture for Separation of Peptides", Anal. Chem., 77, pp. 7131-7136, 2005.

Astorga-Wells, et al., "Formation of Stable Stacking Zones in a Flow Stream for Sample Immobilization in Microfluidic Systems", Anal. Chem., 79, pp. 1057-1063, 2007.

Camacho-Alanis, et al., "Transitioning streaming to trapping in DC insulator-based dielectrophoresis for biomolecules", Sensors and Actuators, B 173, pp. 668-675, 2012.

Chou, et al., "Electrodeless Dielectrophoresis of Single- and Double-Stranded DNA", Biophysical Journal, vol. 83, pp. 2170-2179, Oct. 2002.

Gallo-Villanueva, et al., "DNA manipulation by means of insulator based dielectrophoresis employing direct current electric fields", Electrophoresis, 30, pp. 4195-4205, 2009.

Li, et al., "On-chip DNA preconcentration in different media conductivities by electrodeless dielectrophoresis", Biomicrofluidics 9, 054115, 2015.

Ranchon, et al., "DNA separation and enrichment using electrohydrodynamic bidirectional flows in viscoelastic liquids", Lab Chip, 16, pp. 1243-1253, 2016.

Viefhues, et al., "DNA dielectrophoresis: Theory and applications a review", Electrophoresis, 38, pp. 1483-1506, 2017.

* cited by examiner

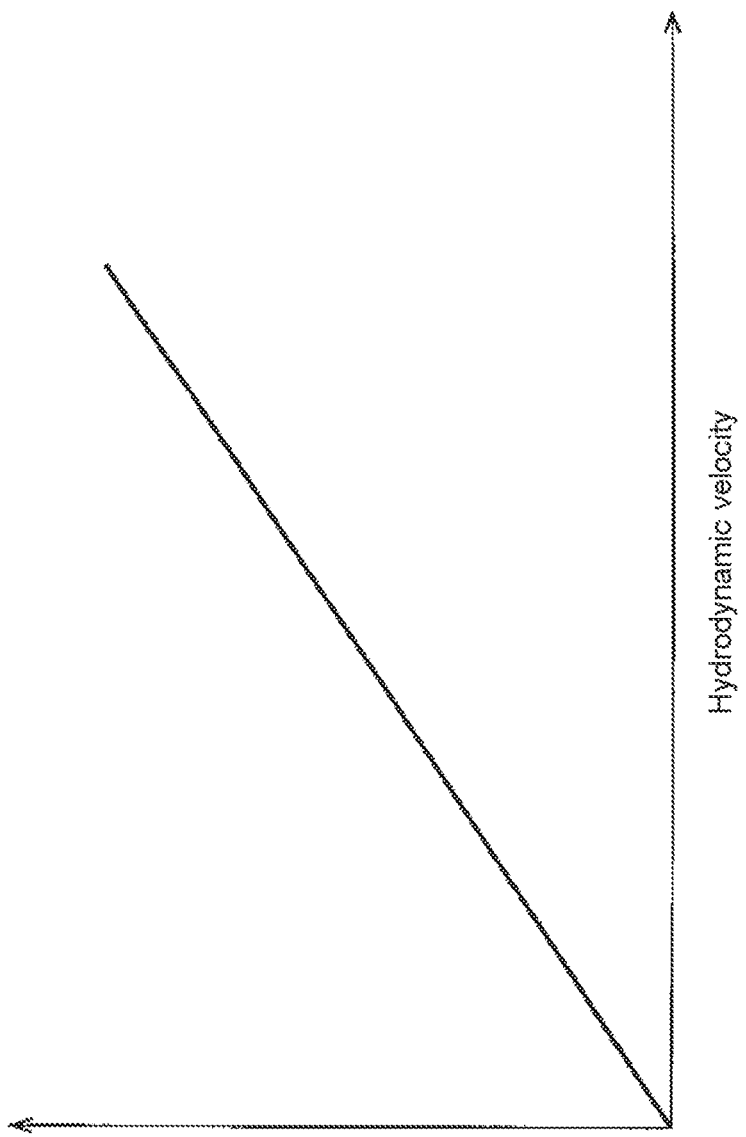

METHOD AND DEVICE FOR CONCENTRATING MOLECULES OR OBJECTS DISSOLVED IN SOLUTION

CROSS-REFERENCE TO RELATED APPLICATIONS

This application is a National Stage of International patent application PCT/EP2015/067826, filed on Aug. 3, 2015, which claims priority to foreign French patent application No. FR 1457544, filed on Aug. 1, 2014, the disclosures of which are incorporated by reference in their entirety.

TECHNICAL FIELD OF THE INVENTION

The invention relates to a process for concentrating electrically charged molecules and objects in solution, and also to a device suitable for the implementation of this process. It comes within the context of an evolution of a technique for the separation of deformable molecules in solution described in WO 2014/020271.

BACKGROUND

Different processes and devices which make it possible to concentrate molecules, in particular DNA molecules, are known in the prior art.

Among these processes and devices, some, in particular those described in U.S. Pat. Nos. 8,753,492, 8,440,063 and 8,783,466, employ ion-selective nanochannels. These techniques exhibit the disadvantage of only being able to be employed with very low flow rates and under certain salinity conditions.

SUMMARY OF THE INVENTION

It is an objective of the invention to provide an alternative to the processes and devices of the prior art.

In particular, one objective of the present invention is to provide a technique which makes it possible to concentrate electrically charged dissolved molecules or generally objects with higher flow rates, suitable for large scale analysis of samples, without restriction with regard to the salinity conditions.

The electrically charged dissolved objects can be deformable and exist in the form of molecules or other more complex objects, such as super molecular assemblies or cells or cell fragments, capable of deforming under the effect of a mechanical stress, such as a hydrodynamic flow. Preferably, the deformability is measured by the Young's modulus of the object, which has to be less than or equal to $10^9$ Pa, or, according to embodiments, less than or equal to $10^8$ Pa. The Young's modulus can be measured by mechanical contact, for example by atomic force microscopy. By way of example, the Young's modulus of DNA typically has a value of approximately 300 MPa and that of mammalian cells from 0.1 to 100 kPa approximately. The electrically charged dissolved objects may also be nondeformable and then exist in particular in the form of electrically charged nanoparticles or nanoobjects.

In the context of the present patent application, the following are in particular regarded as deformable objects: single- or double-strand DNA or RNA molecules comprising at least 20 bases or base pairs (for example of at least 1000); peptides, polypeptides or proteins comprising at least 100 amino acid units (for example at least 200); polymeric carbohydrates or other polymers; karyotic or prokaryotic cells. It has been demonstrated that the invention also operates for nondeformable objects, such as microbeads made of expanded material, such as polystyrene.

Another objective of the present invention is to disclose a technique which, in some embodiments, makes it possible both to concentrate electrically charged molecules or objects and also to separate different electrically charged molecules or objects of a mixture.

Yet another objective of the present invention is to describe a technique, the means of implementation of which are technically very simple.

ACCOUNT OF THE INVENTION

These objectives, and also others which will become apparent subsequently, are achieved by virtue of the invention, which relates to a process for concentrating electrically charged objects in a liquid medium, comprising:

the introduction of a sample containing electrically charged objects into a channel exhibiting a flow axis, a first transverse section orthogonal to the flow axis and at least one second transverse section orthogonal to the flow axis, the minimum dimension of said second section being less than the corresponding dimension of said first section;

the application of a hydrodynamic flow in a direction of said channel in conjunction with the application, in the reverse direction, of an electric field in said channel, making it possible to displace the electrically charged objects in the channel along the flow axis of the first section toward the second section and to halt them and to concentrate them in at least one zone upstream of said second transverse section.

According to the invention, the second transverse section forms a constriction which makes it possible to spatially modulate the hydrostatic and electric fields so as to halt the displacement of the objects at a predetermined spot and to concentrate the objects at this spot. The concentrating of the electrically charged molecules or objects is carried out at said spot subsequent to the accumulation of the electrically charged molecules or objects of the sample which have been halted.

The present invention makes it possible to overcome the disadvantages of the state of the art. In particular, it can be carried out with higher flow rates, whatever the salinity conditions. It more particularly provides a method of concentrating electrically charged molecules and other objects requiring a low concentrating time which is more simple and flexible to carry out than the methods of the state of the art.

It should be noted that the liquid medium is preferably non-newtonian. In the present description, "newtonian fluid" is understood to mean a fluid for which there exists a linear relationship between the applied mechanical stress (force exerted on the fluid per unit of surface area) and the shearing of the fluid (that is to say, velocity gradient of the fluid). A "non-newtonian fluid" is thus a fluid which is not a newtonian fluid.

For example, a non-newtonian fluid according to the invention can have a coefficient of viscosity which depends on the shearing (stationary fluid); or can have an elastic behavior. According to an embodiment, the fluid is viscoelastic.

Preferably, the liquid medium exhibits a viscosity of 1 to 100 cP (centipoises), preferably of 2 to 20 cP and more preferably still of 2 to 10 cP at ambient temperature. Unless otherwise mentioned, the viscosity values mentioned in the patent application are static viscosity values. According to an embodiment, the liquid medium comprises uncharged polymers, preferably chosen from polyvinylpyrrolidone (PVP), poly(ethylene glycol), polyacrylamide and their mixtures.

The term "uncharged" means that the polymers in question have an essentially zero overall electrostatic charge in the abovementioned liquid medium. The presence of such polymers, for example in aqueous solution, makes it possible to render the liquid non-newtonian (for example viscoelastic).

According to one embodiment, the uncharged polymers are present in a concentration by weight of 0.1 to 10%, preferably of 0.5 to 5% and more particularly preferably of 1 to 4%.

Preferably, the concentration of the uncharged polymers is greater than or equal to the critical covering concentration (concentration from which the polymers are in contact).

Advantageously, the uncharged polymers exhibit a (weight-)average molecular weight of 10 to 100 000 kDa, preferably of 50 to 10 000 kDa and more particularly preferably of 100 to 1000 kDa.

According to a preferred alternative form of the process according to the invention, the applied electric field has a value of 10 V/m to 10 000 V/m, preferably of 100 V/m to 5000 V/m and more particularly preferably of 200 V/m to 1000 V/m; and/or the hydrodynamic flow is characterized by a mean velocity of 1 to 10 000 μm/s, preferably of 5 to 5000 μm/s and more particularly preferably of 10 to 1000 μm/s.

Also preferably, the introduction of the electrically charged objects is carried out in an introduction zone of the channel and the displacement of the electrically charged objects is carried out from the introduction zone toward a detection zone of the channel, the process additionally comprising:

the detection of the electrically charged objects arriving in the detection zone.

Advantageously, said electrically charged objects are chosen from the group consisting of: single- or double-stranded DNA or RNA molecules comprising at least 20 bases or base pairs (for example at least 1000); peptides, polypeptides or proteins comprising at least 100 amino acid units (for example at least 200); polymeric carbohydrates or other polymers; karyotic or prokaryotic cells; nanoobjects or nanoparticles.

The invention also relates to a device for concentrating electrically charged objects in a liquid medium, comprising a channel exhibiting a flow axis, the channel being filled with non-newtonian liquid medium; means for application of a hydrodynamic flow in the channel; and means for application of an electric field in the channel, characterized in that said channel exhibits a first transverse section orthogonal to the flow axis and at least one second transverse section orthogonal to the flow axis, the minimum dimension of said second section being less than the corresponding dimension of said first section.

According to an alternative form of the invention, said channel has the shape of a hollow tube of rectangular section exhibiting a lower wall, an upper wall and two side walls, said side walls locally forming at least one constriction.

Preferably, said second section exhibits a minimum dimension lower by at least 10% or by 20% or by 50% or by 95% than the corresponding dimension of said first section.

Advantageously, said side walls of said hollow tube each exhibit a portion forming an angle of between 10° and 65° with said flow axis.

According to another alternative form, said channel is the lumen of a capillary exhibiting at least one constriction.

In this case, said capillary preferably exhibits a square or circular section.

Advantageously, said capillary exhibits a portion forming an angle of between 10° and 65° with said flow axis.

BRIEF DESCRIPTION OF THE DRAWINGS

The invention, and also the different advantages which it exhibits, will be more easily understood by virtue of the description which will follow of embodiments of the invention given with reference to the drawings, in which:

FIGS. 7A, 7B and 7C represent graphs showing the stopping points of molecules as a function of the electrophoretic velocity of molecules and of the hydrodynamic velocity applied or of the electric field and of the flow velocity of the fluid in newtonian and non-newtonian fluids;

DESCRIPTION OF EMBODIMENTS OF THE DEVICE

Figure 1:
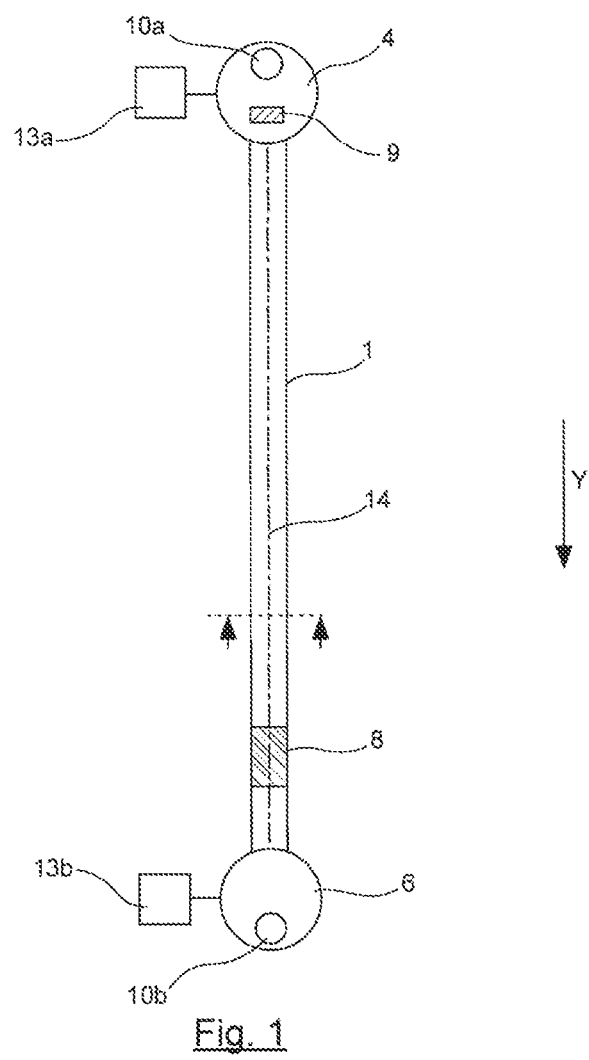
FIG. 1 diagrammatically represents a device according to the invention in top view.
Figure 2:
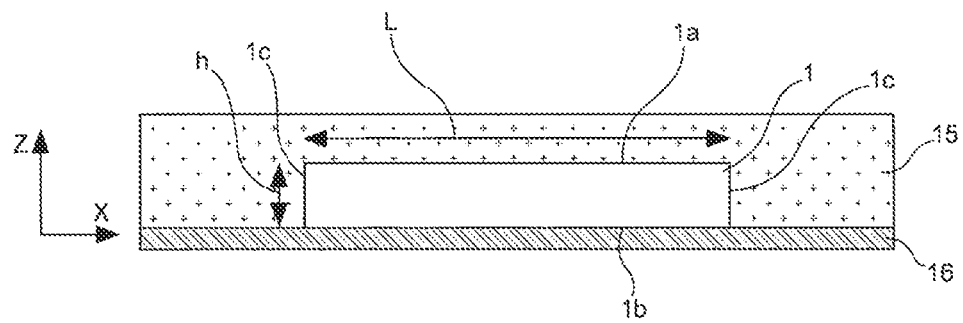
FIG. 2 diagrammatically represents the cross section A-A (magnified) of the device of FIG. 1.

On referring to FIGS. 1 to 5, the device according to the invention comprises a support 16, which can be a strip or thin plate of glass, and a structure 15 exhibiting a recess (for example a microfabricated structure), which can be made of silicon, sealed on the support 16 in a way known per se. For example, it is possible to use film deposition, photolithography, (chemical or plasma) etching and adhesive bonding techniques. Film deposition can be carried out by centrifugation, by thermal oxidation, by chemical vapor deposition or physical vapor deposition (CVD and PVD), by low pressure CVD, by plasma-enhanced CVD, by sputtering, and the like.

The structure 15 (with its recess) and the support 16 define a channel 1. Generally, that is to say over the majority of its length, the channel 1 exhibits the shape of a hollow cylinder of rectangular section defined by an upper wall 1a, a lower wall 1b and side walls 1c. The main axis of the cylinder is the flow axis 14 in the channel 1. Perpendicularly to this flow axis 14, a first transverse section of the channel 1 is defined by a height denoted h and a width denoted L. The height h corresponds to the minimum dimension of the transverse section (it is also the distance between the support 16 and the bottom of the recess of the structure 15) and the width L corresponds to the dimension in the direction orthogonal to that of the height.

Generally, in use, the height h corresponds to the vertical, whereas the width L and the flow axis 14 are in the horizontal plane. The value of h can be chosen as a function of the size of the electrically charged molecules or objects to be concentrated.

The device furthermore comprises an introduction zone 9 of a sample, the electrically charged molecules or objects of which it is desired to concentrate, and a detection zone 8. In the present case, the introduction zone 9 of the sample is located in the reservoir 4 and the sample is injected into the reservoir by virtue of an ancillary device.

Figure 3:
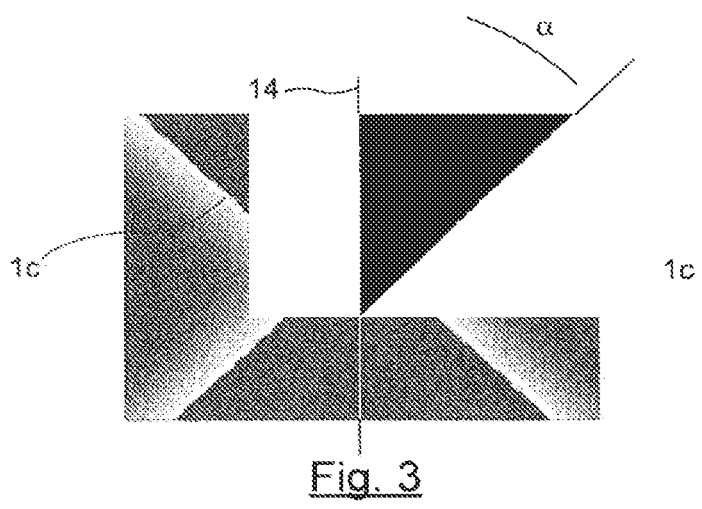
FIG. 3 represents an electron microscopy top view of a first embodiment of a constriction of a device of the type represented in FIGS. 1 and 2.
Figure 4:
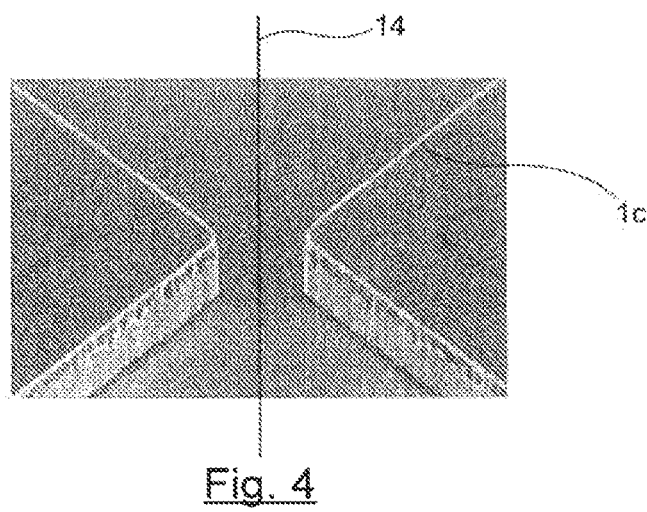
FIG. 4 represents an electron microscopy view in perspective of the constriction represented in FIG. 3.
Figure 5:
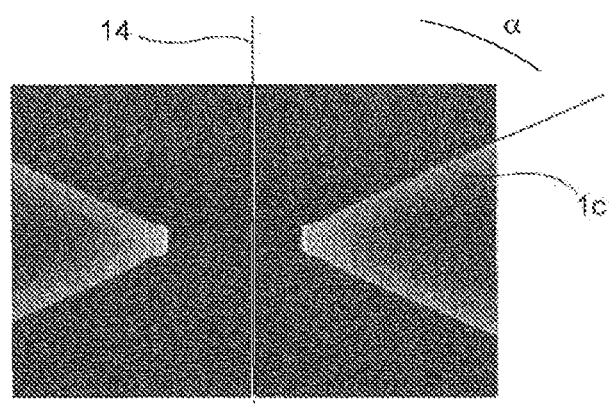
FIG. 5 represents an optical microscopy top view of a second embodiment of a constriction of a device of the type represented in FIGS. 1 and 2.

According to the invention, the channel 1 exhibits a constriction, represented in FIGS. 3 and 4 or 5, in the detection zone 8 defining a second transverse section orthogonal to the flow axis 14, the minimum dimension of which is lower by at least 10% or by 20% or by 50% or by 95% preferably than the corresponding dimension of said first section. According to the invention, the constriction has the effect of spatially modulating the amplitudes of the electric and hydrodynamic fields along the flow axis.

With reference to FIGS. 3 to 5, electron microscopy views of two alternative forms of said constriction 2 are represented. According to the alternative form of FIG. 3 (top view) and FIG. 4 (view in perspective), the side walls 1c of the channel 1 form, at the constriction, an angle α of 45° with the axis 14 of the channel. According to an alternative form of FIG. 5, the side walls of the channel 1 form, at the constriction, an angle of 65°. At the constriction, the width of the channel is reduced to 2.5 μm. Thus, according to the invention, the device is then a span of unvarying height hollowed out in the silicon, the width of which is adjusted.

In use, the channel 1 is filled with a solution which is suitable for electrophoresis, to which have been added components which make it possible to render the fluid non-newtonian. A sample containing electrically charged molecules or objects to be concentrated is introduced into the device in the introduction zone 9.

The migration of the electrically charged molecules or objects in the channel 1 is carried out along the flow axis 14, from the first reservoir 4 toward the second reservoir 6. To do this, a hydrodynamic flow is generated in the channel 1 (in particular by the pressure control means 13a, 13b of the first reservoir 4 and of the second reservoir 6).

In conjunction, an electric field is generated in the channel 1 by means of the electrodes 10a, 10b in the respective reservoirs 4, 6. This electric field is appropriate for applying an electrostatic force to the electrically charged molecules or objects to be concentrated which tends to displace them in the opposite direction to the hydrodynamic flow applied.

Figures 6A, 6B:
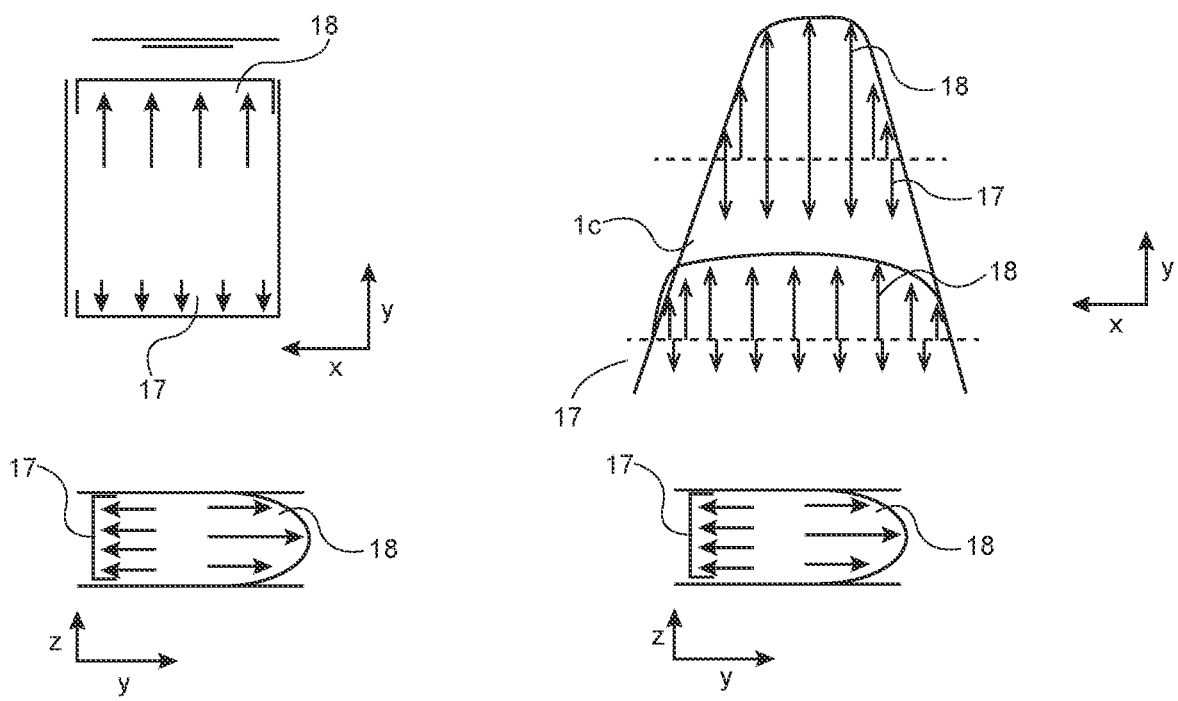
FIGS. 6A and 6B diagrammatically represent the hydrodynamic and electrophoretic force fields in the channel (outside and in the constriction)

With reference to FIG. 6A (the upper part of the figure being a top view and the lower part a side view), during the use of the device outside of the constriction present in the detection zone 8, the electrophoretic force field 17 in the channel 1 is essentially uniform, both in the direction of the flow axis 14 (y axis) and along the height h (z axis) and the width L (x axis) of the channel 1, except in the immediate vicinity of the walls of the channel (over a characteristic length which is negligible with respect to the h and L dimensions). As regards the hydrodynamic force field 18, the latter is uniform in the direction of the flow axis 14 (y axis) and along the width L (x axis), except in the immediate vicinity of the walls of the channel (over a characteristic length which is negligible with respect to the L dimension). On the other hand, it is not uniform along the height h (z axis). Generally, it exhibits a profile of parabolic type characteristic of Poiseuille's law. The aspect ratio L/h of the channel 1 is chosen in order to obtain this configuration of the hydrodynamic force field: this is why the aspect ratio is generally greater than or equal to 1 or greater than or equal to 10 or greater than or equal to 20. The nonuniformity of the hydrodynamic force field 18 along the height h has an influence of the effectiveness of the concentrating of the electrically charged molecules or objects.

The desired hydrodynamic flow profiles (characterized in particular by given mean flow rates and velocity values) are obtained by actuating the respective pressure control means 13a, 13b, so as to generate a pressure difference between the inlet reservoir and the outlet reservoir. For example, in order to generate the hydrodynamic flow providing the migration of the electrically charged deformable molecules or objects to be concentrated from the introduction zone 9 toward the detection zone 8, a pressure difference is generated between the reservoir 4 and the reservoir 6. For example, in view of the geometry of the channels, a pressure difference of 0.01 to 10 bar, preferably of 0.05 to 4 bar and more particularly preferably of 0.1 to 1 bar makes it possible to obtain the desired hydrodynamic flow profiles.

FIG. 6B represents a top view and a side view of the channel in the detection zone comprising the constriction. The upper part of the figure represents a top view of the channel in which the width of the channel decreases along the flow axis due to the presence of the side walls 1c. The lower part represents a side view of the channel, the height of the channel remaining unchanged by the presence of the constriction. With reference to the upper part of the figure, in the (x, y) plane, it is noted that the value of the electrophoretic field increases when the width decreases. Likewise, the profile of the hydrodynamic field changes by conservation of the hydrodynamic flow along the constriction zone. Thus, the variation in the width of the channel induces a variation in the uniform value of the electric field and a variation in the hydrodynamic field profile along the flow axis. On the other hand, in the lower part of the figure, in the (y, z) plane, the hydrodynamic field and the electrophoretic field remain unvarying along the flow axis.

Each molecule is thus subjected, as a function of its position in the detection zone, to different hydrodynamic and electrophoretic fields. The velocity of propagation of each electrically charged molecule or object thus varies during its displacement in the constriction zone along the flow axis.

Figure 7A:
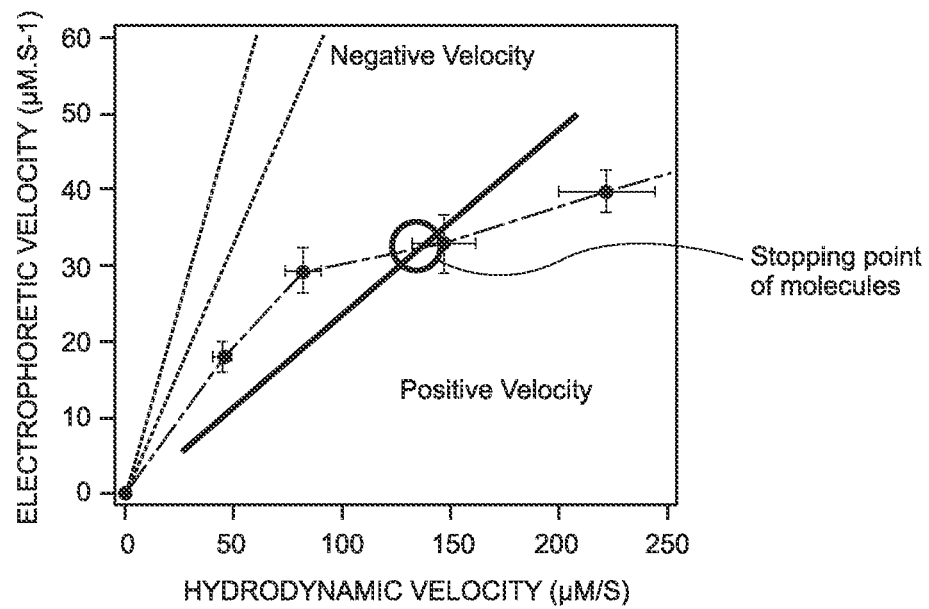

The principle at the basis of the invention is explained with reference to FIGS. 7A, 7B and 7C.

A sample containing DNA molecules comprising 48.5 kpb was introduced into a device of the type of that described above but not exhibiting a constriction, the channel of the device in question exhibiting a section with a minimum dimension of 2 μm. This introduction was carried out so as to observe an unvarying net flow of molecules. The ranges of electrophoretic velocities (ev) and hydrodynamic velocities (hv) were swept by varying the electrophoretic field and also the hydrostatic pressure differential applied to the device. It was found experimentally that the DNA molecule was halted for different pairs of values of hydrodynamic velocity (hv) and electrophoretic velocity (ev) represented on the curve of FIG. 7A as a dotted line. Below this curve, there exists a dominant hydrodynamic effect, corresponding to a positive velocity of the molecules, whereas above this curve, the electrophoretic velocity dominants, corresponding to an overall negative velocity, and the molecules move back. The use according to the invention of a constriction of the channel is symbolized on the graph by the straight line carried passing through the origin which makes it possible to sweep different hydrodynamic and electrophoretic velocity values, as explained with reference to FIG. 6B and to FIGS. 7B and 7C.

The spot where this straight line cuts the curve combining the points for which the velocity is zero (represented by a circle in FIG. 7A) corresponds to a unique stopping zone for a given type of electrically charged molecule or object.

Figure 7B:
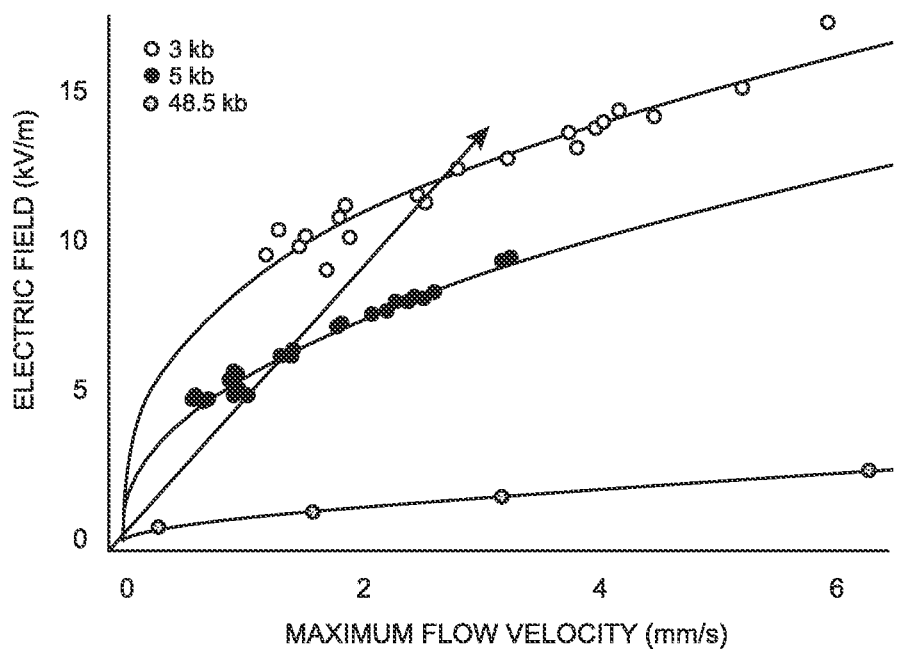

Furthermore, it is found, with reference to FIG. 7B, that, for different samples of DNA of different size, i.e. 3 kb, 5 kb and 48.5 kb, the curves illustrating the stopping parameters of the molecules as a function of the velocity of the fluid and of the electric field applied are different and dependent on the size of the DNA molecule under consideration.

Thus, by sweeping different electrophoretic and hydrodynamic velocity values within the constriction, as represented by the arrow, it is possible to concentrate and to halt different DNA molecules at different spots.

Without wishing to be committed by theory, the inventors consider that, in the presence of a non-newtonian fluid, the shearing of the fluid generates nonlinear couplings between the hydrodynamic flow and the electrophoretic mobility via a transverse force which tends to flatten the molecules toward the wall. This transverse force explains the feeble growth of the response curve of the DNA: the faster the velocity of the flow, the lower the intensity of the electric field necessary to halt a molecule. This force is furthermore dependent on the size of the DNA handled, since a long molecule induces a greater perturbation of the flow and thus an increased non-newtonian effect. Consequently, for given parameters for actuating the fluids (electric field and hydrostatic pressure differential), there exists a series of stopping points of the molecules which make it possible to halt them at a different position along the pipe.

The device according to the invention, in the presence of a non-newtonian fluid, thus makes it possible to concentrate and to separate electrically charged objects of different size, even those of similar mobility (like the devices of the prior art).

In the presence of a newtonian fluid, as will be demonstrated, it is not possible to concentrate electrically charged objects or to separate them.

This is because, in a newtonian fluid, the electrophoretic velocity depends linearly on the electric field according to the relationship $ev(y)=\mu E(y)$, where $\mu$ is the electrophoretic mobility of the DNA which does not depend on the size of the chain, and the hydrodynamic velocity is equal to the mean velocity of the fluid according to the position y of the molecule, i.e. $hv(y)=v(y)$, y being the direction of flow of the fluid in the channel. The molecules will thus be halted when $ev(y)=hv(y)$, i.e. $E(y)=1/\mu \cdot v(y)$. The halting curve, in the case of a non-newtonian fluid, is thus a straight line passing through the origin and of gradient $1/\mu$, as illustrated in FIG. 7C.

The variations in electric field and in hydrodynamic velocity which may be induced by a constriction are now considered. As the electric field E and the flow velocity v have a conservative flux, to a first approximation, it may be considered that:

$$v(y)=S0/S(y)\cdot v0$$

$$E(y)=S0/S(y)\cdot E0$$

where S(y) is the section of the channel in the constriction at the position y; and S0, E0 and v0 denote the values of the section of the channel, of the electric field and of the velocity of the fluid far from the constriction, in the absence of the perturbation induced by the constriction.

The constriction thus makes it possible to sweep an assembly of electric field/flow velocity pairs on a straight line passing through the origin, the gradient of which has a value E0/v0, E0 being the electric field applied in the channel and v0 being the flow velocity in the channel in the absence of constriction.

Thus, in order to be able to halt a molecule, it is necessary to apply, in the absence or in the presence of constriction, experimental conditions such as $E0/v0=1/\mu$. On the other hand, this molecule might not be displaced in the fluid in order to be able to be concentrated since its velocity would be invariant and zero throughout the channel. This is because, in order to be able to concentrate molecules at the same spot, it is necessary for the overall displacement velocity of the molecule ev=hv to decrease before cancelling each out at the stopping point. It will subsequently be seen that, when the sample comprises several electrically charged molecules or objects, for example of similar mobility but of different size, such as DNA molecules, when the parameters, such as the constriction angle and the values of the hydrodynamic and electrophoretic fields applied, are appropriately chosen, it is possible to halt the different molecules or objects at different positions along the flow axis when these molecules or objects are dissolved in a non-newtonian fluid. In this case, the invention also makes it possible to separate the electrically charged molecules or objects of similar mobility. The detection means are not represented in the figures. They can comprise a microscope lens on the side of the support 16 opposite the channel 1, and a detector connected to this, such as a CDD camera. The electrically charged individual molecules or individual objects can thus be detected on the acquired image, and an overall intensity measurement in the detection zone 8 or a portion of the latter as a function of the time can be carried out.

Means for analysis of the measurements and of presentation of the data obtained can be combined with this device.

The device can also be incorporated in a lab-on-chip, comprising, for example, other channels, reservoirs and/or electrodes similar to those described above. For example, the lab-on-chip can comprise a chemical or biochemical reaction device coupled downstream to the separation device according to the invention. Thus, the use of the concentrating process according to the invention makes it possible to analyze the products from a chemical or biochemical reaction carried out in the lab-on-chip.

The lab-on-chip can also comprise means for collecting fractions corresponding to the different electrically charged molecules or objects concentrated. These collecting means can be provided downstream of the detection zone 8. Alternatively, they can replace the detection zone 8, in which case the device is used for a solely preparative purpose.

These collecting means can be provided in combination with the abovementioned chemical or biochemical reaction device, or without it.

EXAMPLES

A standard buffer solution for the electrophoresis of DNA, consisting of 80 mM of Tris-HCl, 80 mM of boric acid, 5 mM of ethylenediaminetetraacetic acid, 0.5 µM of dithiothreitol, to which 2% by weight of 360 kDa PVP have been added, was used to dilute different DNA samples. As described above, the introduction of the PVP makes it possible to render the buffer solution non-newtonian. Generally, different samples of DNA of different sizes were diluted in this buffer solution in a proportion of 1 to 10 ng/µl of nucleic acids.

The nucleic acids present in the DNA fragments are rendered fluorescent by labeling using an intercalating agent (YOYO(R), Molecular Probes) in a proportion of one probe per 4 base pairs.

The device used for separating and analyzing this population of molecules is as represented in FIG. 1. The channel 1 has a width of 100 µm and a height of 2 µm. In its narrowest zone formed by the constriction, also known as second transverse section, the channel 1 has a width of 2 µm and a height of 2 µm. The introduction zone 9 and the detection zone 8 are separated by 5 mm. 200 µl of buffer solution not containing sample are positioned in the reservoirs 4 and 6 of the channel 1. A flow of solution from the reservoir 4 toward the reservoir 6 is created by adjusting the pressures in order to make possible the saturation of the surfaces made of PVP, for 30 min.

Example 1

Sample Containing Two Types of DNA Having Small Sizes and Large Sizes

In this example, the invention is used to separate and concentrate Lambda DNA comprising 48.5 kpb and PhiX174 DNA comprising 5.4 kpb present in a buffer solution as described above.

Figure 8:
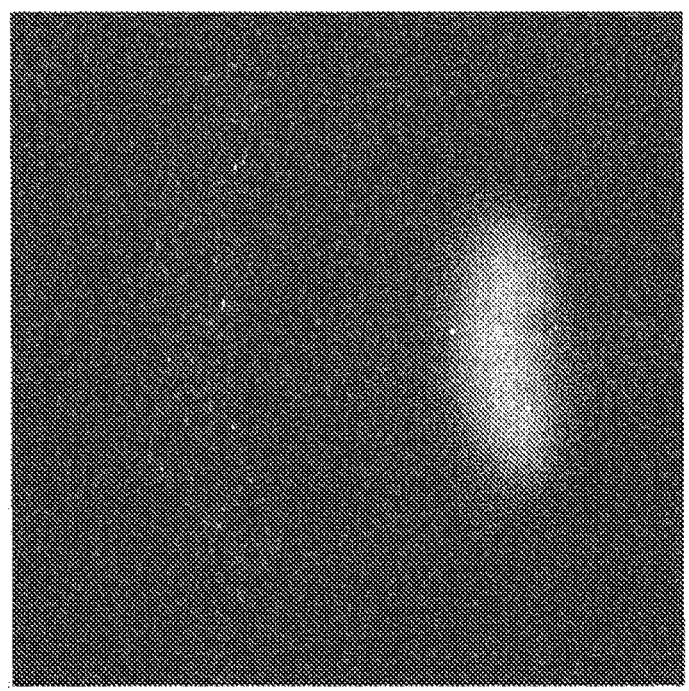
FIG. 8 represents a fluorescence microscopy photograph of two DNA populations different in their size separated and concentrated by virtue of a device of the type of that described with reference to FIGS. 1 to 4.

An overall pressure difference of 100 mbar and an overall voltage difference of 40 V were used with crossed hydrodynamic and electrophoretic flows, that is to say flows oriented along the flow axis but along opposite axes. After waiting for one minute, a fluorescence microscopy photograph was taken. This photograph is represented in FIG. 8. By virtue of the constriction, the molecules have been stopped in a zone upstream of the constriction. They accumulate because the hydrodynamic effects dominate before the stopping point, which results in a positive velocity, and they move back downstream. The device then constitutes both a concentrator and a separator as the stopping point depends on the size of the molecules. In FIG. 8, there is thus seen a cloud corresponding to the Lambda DNA molecules separated from another cloud corresponding to the PhiX174 DNA molecules. After using the device for one minute, a factor 10 of concentrating these two different DNAs was obtained. This factor can be further improved by increasing the hydrodynamic flow.

Example 2

Sample Containing Three Types of DNA

Figure 9:
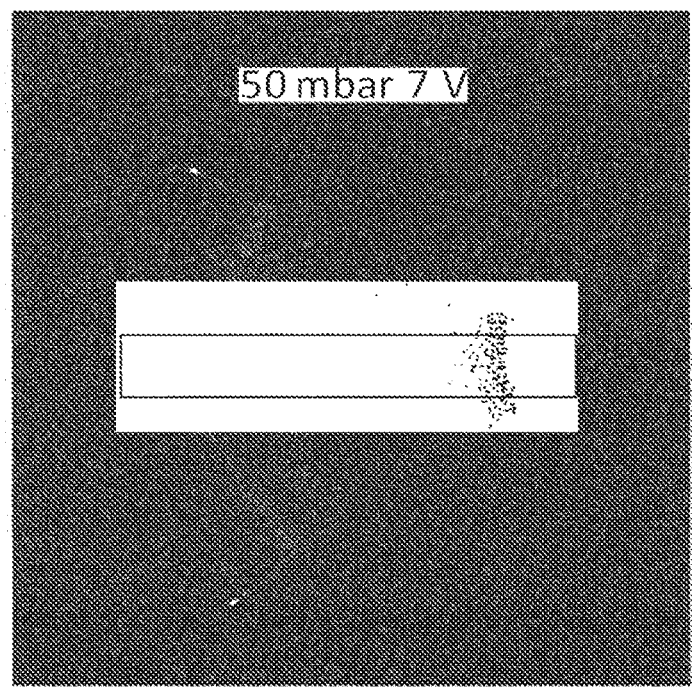
FIG. 9 represents a fluorescence microscopy photograph of three DNA types separated and concentrated by virtue of a device of the type of that described with reference to FIGS. 1 to 4.
Figure 10:
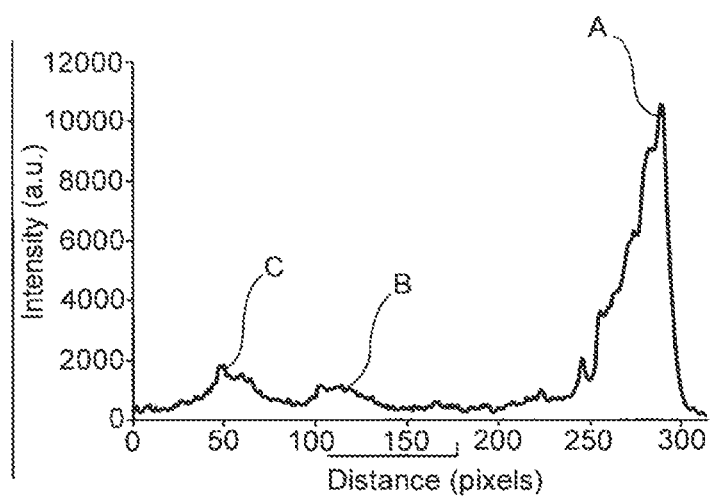
FIG. 10 is a graph showing the light intensity of the points appearing in the context represented in FIG. 9.

The invention has also been used with a sample containing three types of DNA, of 15 kbp, 35 kbp and 49 bp. An overall pressure difference of 50 mbar and an overall voltage difference of 7 V were used with crossed hydrodynamic and electrophoretic flows. After waiting for 100 seconds, a fluorescence microscopy photograph was taken. This photograph is represented in FIG. 9. The light intensity of three clouds corresponding to the concentrating of the three types of DNA molecules was evaluated. The corresponding results are plotted on the graph represented in FIG. 10. This graph shows three peaks A, B and C corresponding to the three separated and concentrated types of DNA.

Example 3

Sample Containing DNAs Having Small Sizes

The invention has also been used on a 1 kpb DNA ladder molecular weight label comprising 500 to 10 000 base pairs.

An overall pressure difference of 100 mbar and an overall voltage difference of 40 V were used with crossed hydrodynamic and electrophoretic flows.

Figure 11:
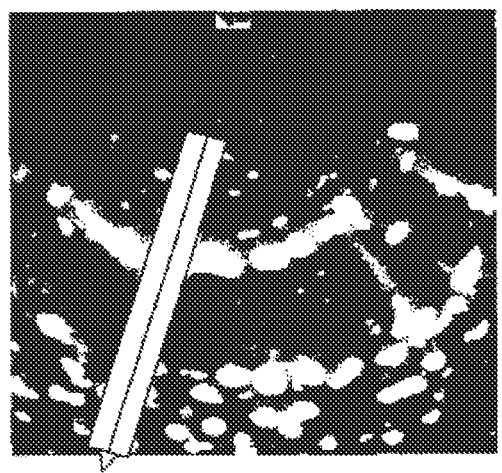
FIG. 11 represents a fluorescence microscopy photograph of different DNAs separated and concentrated by virtue of a device of the type of that described with reference to FIGS. 1 to 4.
Figure 12:
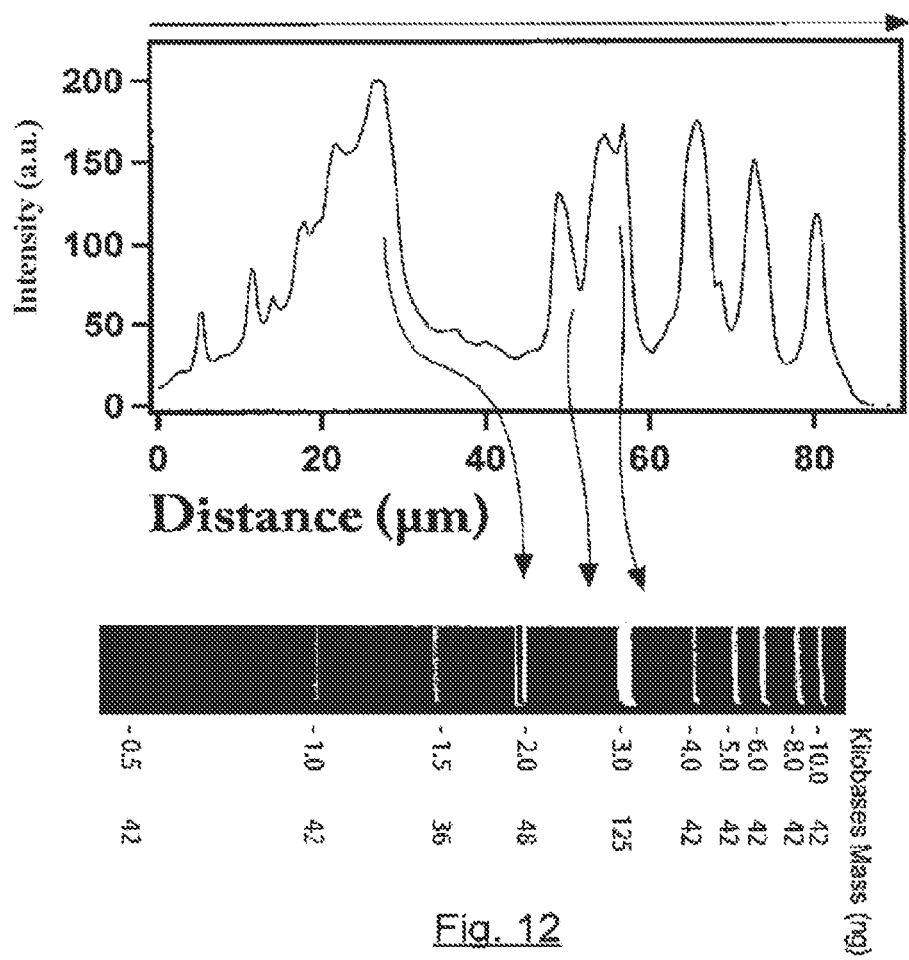
FIG. 12 is a graph showing the light intensity of the points appearing in the context represented in FIG. 11.

After waiting for 17 seconds, a fluorescence microscopy photograph was taken. This photograph is represented in FIG. 11. The light intensity of the zone included in the frame plotted on this figure was measured. The corresponding results are plotted on the graph represented in FIG. 12. These results show a separation and a concentration corresponding to the different DNAs constituting the label, such as those represented on a lower scale, and implies the invention can be used for the application of short-sized DNAs.

Example 4

Sample Containing Microbeads

Figure 13:
FIG. 13 represents a fluorescence microscopy photograph of polystyrene beads with a diameter of 100 nm concentrated by virtue of a device of the type of that described with reference to FIGS. 1 to 4.

The invention has also been used with a sample containing fluorescent polystyrene microbeads with a diameter of 100 nm (Fluorospheres™, Invitrogen). The deformability of such microbeads is fairly low, its Young's modulus being of the order of 3 GPa. The microbeads were diluted in a solution comprising an abovementioned buffer solution and 2% by weight of 360 kDa PVP. The same device as that described above for the separation and the concentration of the DNA was used. In this example, 200 µl of solution based on TBE and on PVP, such as that described above, were used. An overall pressure difference of 150 mbar and an overall voltage difference of 40 V were used with crossed hydrodynamic and electrophoretic flows. After waiting for 18 seconds, a fluorescence microscopy photograph was taken. This photograph is represented in FIG. 13. The microbeads are concentrated in a less homogeneous zone than in the case of DNA molecules. The dispersion observed in the distribution of the microspheres can be explained by the nonhomogeneity of the sample observed with respect to the DNA populations, the number of base pairs of which is fixed. Thus, it is demonstrated that a separation and a concentration of electrically charged objects with a Young's modulus of greater than or equal to $10^9$ Pa is also possible. Thus, the range of application of the invention is not limited to the concentration and to the separation of DNA molecules but can be extended to any type of electrically charged object of the type of those described above.

It should be noted that, according to the composition of the sample and the electrophoretic and hydrodynamic field values, some electrically charged molecules or some electrically charged objects can maintain a positive displacement velocity during their displacement along the flow axis of the channel. These molecules are thus not halted upstream of the constriction and can be collected downstream. The device according to the invention can thus also be used as device for filtering molecules.

In the different embodiments and examples represented here, the channel had the shape of a hollow tube of rectangular section, one of the faces of which is transparent so as to make possible the optical detection of the electrically charged molecules or objects.

It is also possible to consider a channel formed by the lumen of a capillary, that is to say of a tubular structure, of preferably square or circular section, made of a transparent material, such as, for example, glass.

It should furthermore be noted that, in other embodiments, the constriction can consist of walls which approach the flow axis in a nonlinear fashion.

The invention claimed is:

1. A process for concentrating electrically charged objects in a non-newtonian liquid medium, comprising:
the introduction of a sample containing electrically charged objects into a channel exhibiting a flow axis, a first transverse section orthogonal to the flow axis and at least one second transverse section orthogonal to the flow axis, the minimum dimension of said second transverse section being less than the corresponding dimension of said first transverse section, wherein temperatures within the first transverse section and within the second transverse section are at ambient temperature, the electrically charged objects being intended to migrate along the flow axis from a first reservoir to a second reservoir;
the application of a hydrodynamic flow, in the first and second reservoirs by means of pressure control means of the first reservoir and of the second reservoir, in a direction of said channel in conjunction with the application, in the reverse direction, of a non-alternating electric field in said channel by means of electrodes in the first and second reservoirs, making it possible to displace the electrically charged objects in the channel along the flow axis of the first transverse section toward the second section and to halt them and to concentrate them in at least one zone upstream of said second transverse section.

2. The process as claimed in claim 1, wherein the liquid medium comprises uncharged polymers.

3. The process as claimed in claim 2, wherein the uncharged polymers are chosen from polyvinylpyrrolidone, poly(ethylene glycol), polyacrylamide and their mixtures.

4. The process as claimed in claim 3, wherein the uncharged polymers are present in a concentration by weight of 0.1 to 10%, preferably of 0.5 to 5% and more particularly preferably of 1 to 4%.

5. The process as claimed in claim 1, wherein:
the applied electric field has a value of 10 V/m to 10 000 V/m, preferably of 100 V/m to 5000 V/m and more particularly preferably of 200 V/m to 1000 V/m; and/or
the hydrodynamic flow is characterized by a mean velocity of 1 to 10 000 µm/s, preferably of 5 to 5000 µm/s and more particularly preferably of 10 to 1000 µm/s.

6. The process as claimed in claim 1, wherein:
the introduction of the electrically charged objects is carried out in an introduction zone of the channel and the displacement of the electrically charged objects is carried out from the introduction zone toward a detection zone of the channel, the process additionally comprising:
the detection of the electrically charged objects arriving in the detection zone.

7. The process as claimed in claim 1, wherein said electrically charged objects are chosen from the group consisting of: single- or double-stranded DNA or RNA molecules comprising at least 20 bases or base pairs; peptides, polypeptides or proteins comprising at least 100 amino acid units; polymeric carbohydrates or other polymers; karyotic or prokaryotic cells; nanoobjects or nanoparticles.

8. A device for concentrating electrically charged objects in a liquid medium, comprising:
a channel exhibiting a flow axis, the channel being filled with a non-newtonian liquid medium, the electrically charged objects being intended to migrate along the flow axis from a first reservoir to a second reservoir;
means for application of a hydrodynamic flow in the first and second reservoirs by means of pressure control means of the first reservoir and of the second reservoir; and
means for application of a non-alternating electric field in the channel by means of electrodes in the first and second reservoirs,
wherein said channel exhibits a first transverse section orthogonal to the flow axis and at least one second transverse section orthogonal to the flow axis, the minimum dimension of said second transverse section being lower than the corresponding dimension of said first transverse section, wherein a first temperature within the first transverse section and a second temperature within the second transverse section are at ambient temperature.

9. The device as claimed in claim 8, wherein said channel has the shape of a hollow tube of rectangular section exhibiting a lower wall, an upper wall and two side walls, said side walls locally forming at least one constriction.

10. The device as claimed in claim 8, wherein said second section transverse exhibits a minimum dimension lower by at least 10% or by 20% or by 50% or by 95% than the corresponding dimension of said first transverse section.

11. The device as claimed in claim 9, wherein said side walls of said hollow tube each exhibit a portion forming an angle of between 10° and 65° with said flow axis.

12. The device as claimed in claim 8, wherein said channel is a lumen of a capillary exhibiting at least one constriction.

13. The device as claimed in claim 12, wherein said capillary exhibits a square or circular section.

14. The device as claimed in claim 12, wherein said capillary exhibits a portion forming an angle of between 10° and 65° with said flow axis.

15. The process as claimed in claim 1, wherein said channel has the shape of a hollow tube of rectangular section exhibiting a lower wall, an upper wall and two side walls, said side walls locally forming at least one constriction, and said side walls of said hollow tube each exhibit a portion forming an angle of between 10° and 65° with said flow axis.

16. The process as claimed in claim 1, wherein said channel has the shape of a hollow tube of rectangular section exhibiting a lower wall, an upper wall and two side walls, said side walls locally forming at least one constriction, said channel is a lumen of a capillary exhibiting at least one constriction, and said capillary exhibits a portion forming an angle of between 10° and 65° with said flow axis.

* * * * *